United States Patent [19]

Cobb

[11] Patent Number: 4,716,254

[45] Date of Patent: Dec. 29, 1987

[54] PREPARATION OF AROMATIC IODINE COMPOUNDS

[75] Inventor: Raymond L. Cobb, Bartlesville, Okla.

[73] Assignee: Phillips Petroleum Company, Bartlesville, Okla.

[21] Appl. No.: 882,575

[22] Filed: Jul. 7, 1986

[51] Int. Cl.$^4$ ............................................. C07C 17/12
[52] U.S. Cl. ..................................... 570/147; 570/206
[58] Field of Search ............... 570/206, 147, 190, 143, 570/191

[56] References Cited

U.S. PATENT DOCUMENTS

| | | | |
|---|---|---|---|
| 2,607,802 | 8/1952 | Britton et al. | 570/206 |
| 2,637,745 | 5/1953 | Schwenk et al. | 260/520 |
| 2,907,799 | 10/1959 | Hughes et al. | 585/427 |
| 3,013,079 | 12/1961 | Pearson et al. | 260/592 |
| 3,226,447 | 12/1965 | Bing et al. | 260/650 |
| 3,317,618 | 5/1967 | Haszeldine | 570/143 |
| 3,576,893 | 4/1971 | Baird | 260/651 |
| 3,911,033 | 10/1975 | Schaffner et al. | 570/191 |
| 4,158,674 | 6/1979 | Morris | 260/650 R |

OTHER PUBLICATIONS

Journal of the Chemical Society, 1957, Part II, pp. 1823-1829; article by G. Oláh et al.
Beilsteins Handbuch der Organischen Chemie, Drittes Ergaenzungswerk, Fuenfter Band, 1964, pp. 578-579.

Primary Examiner—Donald B. Moyer
Assistant Examiner—Joseph A. Boska
Attorney, Agent, or Firm—K. K. Brandes

[57] ABSTRACT

Monohalobenzene compounds are iodinated with an iodination reagent selected from the group consisting of (i) iodine monochloride and (ii) $I_2/Cl_2$ mixtures having a mol ratio of about 1:3-5:1, in the presence of a catalyst selected from the group consisting of $MoCl_5$, $FeCl_3$, lanthanide chlorides and mixtures thereof. Preferably one of chlorobenzene and fluorobenzene is at least partially converted to at least one of para-iodochlorobenzene and para-iodofluorobenzene. Various other aromatic compounds, preferably di- and trichlorobenzene, xylenes, nitrobenzene and ethyl benzoate, are iodinated with an iodination reagent selected from the group consisting of (i) iodine monochloride and (ii) $I_2/Cl_2$ mixtures having a mol ratio of about 1:3-5:1, in the presence of a catalyst comprising $FeCl_3$ and, optionally, a lanthanide chloride.

14 Claims, No Drawings

4,716,254

PREPARATION OF AROMATIC IODINE COMPOUNDS

BACKGROUND OF THE INVENTION

In one aspect, this invention relates to a process for preparing para-iodohalobenzene compounds such as p-iodofluorobenzene and p-iodochlorobenzene. In another aspect, this invention relates to the iodination of aromatic compounds in the presence of transition metal halide catalysts.

The iodination of aromatic compounds, in particular para-halbenzene compounds, is known. However, there is an ever present need to develop new processes to produce iodo-compounds, in particular para-iodobenzene compounds, at a higher selectivity than achieved by known processes.

SUMMARY OF THE INVENTION

It is an object of this invention to convert halobenzene compounds to para-iodohalobenzene compounds. It is another object of this invention to convert chlorobenzene to p-iodochlorobenzene (1-iodo-4-chlorobenzene) at high selectivity. It is a further object of this invention to convert fluorobenzene to p-iodofluorobenzene (1-iodo-4-fluorobenzene) at high selectivity. It is a still further object of this invention to iodinate dihalobenzene compounds, trihalobenzene compounds, alkyl-substituted benzene compounds, nitro-substituted benzene compounds, carboxylated benzene compounds and similar compounds, in the presence of transition metal halide catalysts. It is still another object of this invention to use p-iodohalobenzene compounds for preparing p,p'-dihalobiphenyl compounds.

In accordance with this invention, an iodination process comprises the step of contacting (a) a feed stream comprising at least one monohalobenzene compound with (b) an iodination reagent selected from the group consisting of (i) iodine chloride and (ii) mixtures of free iodine and free chlorine having an $I_2:Cl_2$ mol ratio in the range of from about 1:3 to about 3:1, and (c) a catalyst composition comprising (preferably consisting essentially of) at least one substance selected from the group consisting of molybdenum(v) chloride, iron(III) chloride, lanthanide chlorides, and mixtures thereof, under such iodination conditions as to obtain a product comprising at least one para-iodohalobenzene compound.

In a preferred embodiment of this invention, the monohalobenzene compound is chlorobenzene, and the product comprises p-iodochlorobenzene. In another preferred embodiment, the monohalobenzene compound is fluorobenzene, and the product comprises p-iodofluorobenzene. In a further preferred embodiment, the catalyst composition consists essentially of either $MoCl_5$ alone, or $FeCl_3$ alone, or $CeCl_3$ alone, or a mixture of $FeCl_3$ and $CeCl_3$, or a mixture of $FeCl_3$ and $SmCl_3$. Preferably, the formed product comprises a greater amount of para-iodohalobenzene than of ortho-iodohalobenzene. Also preferably, the iodination reagent (ii) has a an $I_2:Cl_2$ mol ratio in the range of from about 1:2 to about 2:1.

In another embodiment of this invention, the iodination process as described above comprises the additional steps of separating at least one of p-iodofluorobenzene and p-iodochlorobenzene from the iodination product and then contacting at least one of p-iodofluorobenzene and p-iodochlorobenzene with a metal selected from the group consisting of copper, nickel and cobalt (preferably Cu) under such reaction conditions as to obtain a reaction product comprising at least one of p,p'-dichlorobiphenyl and p,p'-difluorobiphenyl.

Also in accordance with this invention, an iodination process comprises the step of contacting (a) a feed stream comprising at least one aromatic feed compound selected from the group consisting of benzene, alkyl-substituted benzenes, naphthalene, alkyl-substituted naphthalenes, biphenyl, alkyl-substituted biphenyls, dihalobenzenes, alkyl-substituted dihalobenzenes, trihalobenzenes, alkyl-substituted trihalobenzenes, nitrobenzene, alkyl-substituted nitrobenzene, phenols, alkyl-substituted phenols, phenol ethers, alkyl-substituted phenol ethers, benzoic acid, alkyl-substituted benzoic acid, esters of benzoic acid and esters of alkyl-substituted benzoic acid, with (b) an iodination reagent selected from the group consisting of (i) iodine monochloride and (ii) mixtures of free iodine and free chlorine having an $I_2:Cl_2$ mol ratio in the range of from about 1:3 to about 3:1, and (c) a catalyst composition comprising iron(III) chloride, under such reaction conditions as to substitute at least one hydrogen atom by an iodine atom in an aromatic ring of at least a portion of said at least one aromatic feed compound.

Preferably, the aromatic feed compound is selected from the group consisting of 1,2-dichlorobenzene, 1,2,4-trichlorobenzene, o-, m- and p-xylenes, nitrobenzene and ethyl benzoate. Also preferably, the iodination reagent (ii) has an $I_2:Cl_2$ mol ratio in the range of from about 1:2 to about 2:1. Preferably, catalyst composition (c) additionally comprises a lanthanide chloride, more preferably $SmCl_3$.

DETAILED DESCRIPTION OF THE INVENTION

Iodination of Monohalobenzene Compounds

Any feed stream which contains a monohalobenzene compound or a mixture of two or more such compounds can be used in the iodination process of this invention. The feed stream may contain a suitable diluent. Preferably, undiluted liquid chlorobenzene or fluorobenzene is used as feed. Other, presently less preferred, monohalobenzene compounds include bromobenzene, 1-chloro-2-methylbenzene, 1-chloro-3-methylbenzene, 1-chloro-2-ethylbenzene, 1-chloro-3-ethylbenzene, 1-chloro-2,5-dimethylbenzene, 1-fluoro-2-methylbenzene, 1-fluoro-3-methylbenzene, 1-fluoro-2-ethylbenzene, 1-fluoro-3-ethylbenzene, 1-fluoro-2,5-dimethylbenzene and the like.

The feed stream which contains monohalobenzene compound(s) can be contacted with the iodination reagent and the catalyst composition, in accordance with this invention, in any suitable manner. The iodination process of this invention can be carried out as a continuous process or as batch process, preferably with agitation (e.g., by using mechanical stirring means or static mixing means).

The catalyst, which has a high selectivity for producing para-iodohalobenzene compounds (i.e., 1-iodo-4- halobenzene compounds), when employed in the iodination process of this invention can be MoCl$_5$; or FeCl$_3$; or a lanthanide chloride (such as LaCl$_3$, CeCl$_3$, PrCl$_3$, NdCl$_3$, SmCl$_3$, GdCl$_3$, TbCl$_3$ and the like; preferably CeCl$_3$ or SmCl$_3$), or, preferably, a mixture of FeCl$_3$ with one or more lanthanide chlorides, more preferably a mixture of FeCl$_3$ with CeCl$_3$ or a mixture of FeCl$_3$ with SmCl$_3$. When such a mixture is employed, the weight ratio of FeCl$_3$ to the lanthanide chloride will generally be in the range of from about 1:10 to about 20:1, preferably about 1:2 to about 10:1.

The iodination reagent can be a mixture of free iodine and free chlorine having a mol ratio of I$_2$:Cl$_2$ in the range of from about 1:3 to about 3:1, preferably about 1:2 to about 2:1; or (presently less preferably) the iodination agent can be ICl. When a mixture of I$_2$ and Cl$_2$ is employed, these two elements can be introduced into a reactor, where the iodination of the feed compound occurs, in any order. I$_2$ can be charged as a separate stream simultaneously with Cl$_2$ (liquid or gas) into the reactor, which generally already contains the feed and catalyst. Or I$_2$ can be premixed with the feed and catalyst composition, and Cl$_2$ can be introduced into the above mixture, preferably after heating of the mixture to the reaction temperature.

In a continuous operation, preferably the feed stream (containing at least one monohalobenzene compound) is mixed with iodine, and this mixture is introduced concurrently with a stream of catalyst composition and a liquid or gaseous (preferably gaseous) chlorine stream into a reactor. These three streams are then mixed by mechanical stirring or static mixing means while they flow through the reactor in any direction (downflow, upflow or horizontal).

The mol ratio of the monohalobenzene compound contained in the feed stream to I$_2$ (or if used, ICl) is generally in the range of from about 100:1 to about 1:3, preferably in the range of from about 10:1 to about 1:1. The mol ratio of the monohalobenzene compound to the catalyst composition is generally in the range of from about 200:1 to about 2:1, preferably about 100:1 to about 10:1.

Any suitable reaction conditions can be employed in the iodination process of this invention. The reaction temperature can be in the range of from about 0° C. to about 200° C., preferably about 10° C. to about 150° C. The reaction pressure can be subatmosphereic, atmospheric (i.e., about 1 atm) or superatmospheric. Generally, the reaction pressure is about atmospheric. Any suitable reaction time, i.e., the time of intimate contact between feed, iodination reagent and catalyst composition, can be employed. The reaction time can range from about 1 second to about 20 hours, preferably about 0.01 hours to about 2 hours.

Any formed product, preferably 1-iodo-4-chlorobenzene or 1-iodo-4-fluorobenzene, can be separated from the product (i.e., unreacted monohalobenzene compound, unreacted iodination reagent, the catalyst composition and other formed product components) in any suitable manner by any suitable separation means, preferably by fractional distillation. Unreacted monohalobenzene compound can be recycled to the reactor.

The preferred, separated product component, 1-iodo-4-chlorobenzene or 1-iodo-4-fluorobenzene, can then be contacted in any suitable manner with a suitable metal, preferably copper, under such reaction conditions as to form 4,4'-dichlorobiphenyl and 4,4'-difluorobiphenyl, respectively. The metal (such as Cu) binds two iodine atoms from two different molecules of 1-iodo-4-chlorobenzene (para-iodochlorobenzene) or 1-iodo-4-fluorobenzene (para-iodofluorobenzene) and forms a metal iodide (such as CuI$_2$). This reaction with a suitable metal is generally carried out at an elevated temperature (preferably about 150°-250° C.), at any suitable pressure (preferably about atmospheric), for any suitable time period (preferably about 1-20 hours). The above-described formed compound, 4,4'-dichlorobiphenyl or 4,4'-difluorobiphenyl, can be separated in any manner from the above metal-containing reaction mixture, and can be converted to poly(biphenylene sulfide) in any suitable manner, e.g., substantially in accordance with the procedure described in U.S. Pat. No. 3,354,129.

Iodination of Other Aromatic Compounds

Any feed stream which contains at least one (i.e., one, two or more) suitable aromatic feed compound can be used in the iodination process of this invention. The feed may contain a suitable diluent. Preferably, undiluted, liquid aromatic feed compound is used.

Non-limiting examples of suitable aromatic feed compounds are benzene, toluene, o-xylene, m-xylene, p-xylene, ethylbenzene, naphthalene, biphenyl, 1,2-difluorobenzene, 1,2-dichlorobenzene, 1,2-dibromobenzene, 1,3-difluorobenzene, 1,3-dichlorobenzene, 1,4-difluorobenzene, 1,4-dichlorobenzene, 1,2,4-trichlorobenze, 1,3-dichloro-2-methylbenzene, nitrobenzene, 2-methyl-1-nitrobenzene, 3-methyl-1-nitrobenzene, 3,5-dimethyl-1-nitrobenzene, phenol, cresols, phenyl methyl ether, phenyl ethyl ether, diphenyl ether, methyl cresol ether, benzoic acid, tolyl acid, benzyl carboxylic acid, methyl benzoate, ethyl benzoate, propyl benzoate, propyl tolyate and the like, and mixtures thereof.

The feed stream, which contains at least one suitable organic feed compound, can be contacted with the iodination reagent and the catalyst composition in accordance with this invention in any suitable manner. The iodination process of the embodiment of this invention can be carried out as a continuous process or as a batch process, preferably with agitation (by mechanical stirring or static mixing).

The catalyst comprises FeCl$_3$ and, preferably, additionally at least one lanthanide chloride such as LaCl$_3$, CeCl$_3$, NdCl$_3$, SmCl$_3$, EuCl$_3$, GdCl$_3$, TbCl$_3$, DyCl$_3$, ErCl$_3$ and the like, preferably at least one of CeCl$_3$ and SmCl$_3$. The weight ratio of FeCl$_3$ to the lanthanide chloride (when present) will generally be in the range of from about 1:10 to about 20:1, preferably from about 1:2 to about 10:1.

The iodination reagents are the same as those described above for the iodination of monohalobenzene compounds. Also, the description of the introduction of I$_2$ and Cl$_2$, as described above for the iodination of mono-halobenzene compounds can be applied for the iodination of other aromatic feed compounds. The mol ratio of the aromatic feed compound to I$_2$ (or if used, ICl) is generally in the range of from about 100:1 to about 1:3, preferably about 10:1 to about 1:1. The mol ratio of the aromatic feed compound(s) to the entire catalyst composition is generally in the range of from about 200:1 to about 2:1, preferably about 100:1 to about 10:1.

Any suitable reaction conditions can be employed in the iodination of organic feed compounds in the process of this invention. The reaction temperature generally is in the range of from about 0° C. to about 180° C., preferably about 10° C. to about 140° C. The pressure can be atmospheric (preferred), subatmospheric or superatmospheric. The reaction time can be in the range of from about 1 second to about 20 hours, preferably about 0.01 to about 3 hours.

Non-limiting examples of compounds that can be formed in the iodination of suitable aromatic feed com- 250° C. Typical retention times under these conditions were 9.50 minutes for chlorobenzene, 14.4–15.2 minutes for dichlorobenzenes, 19.2 minutes for para-iodochlorobenzene and 19.6 minutes for ortho-iodochlorobenzene. No meta-iodo-compounds were detected.

All metal halide catalysts employed were anhydrous and had been stored in a desiccator under nitrogen. Pertinent test results are summarized in Table I.

TABLE 1

| Run | Catalyst | Temp. (°C.) | Mol Ratio of $I_2:Cl_2$ | % Conversion of Chlorobenzene | % Selectivity[1] to I—Ph—Cl[2] | % Selectivity[1] to Cl—Ph—Cl[3] | Ratio of p- to o-I—Ph—Cl[4] |
|---|---|---|---|---|---|---|---|
| 1 (Control) | $AlCl_3$ | 45–50 | 1.2:1 | 16 | 48.0 | 52.0 | 5.8 |
| 2 (Control) | $AlCl_3$ | 45–50 | 0.8:1 | 22 | 42.0 | 58.0 | 8.0[5] |
| 3 (Control) | $SbCl_5$ | ~30 | 0.9:1 | 18 | 32.6 | 67.4 | 5.2 |
| 4 (Control) | $SbCl_5$ | ~60 | 0.9:1 | 18 | 42.7 | 57.3 | 4.5 |
| 5 (Invention) | $FeCl_3$ | ~40 | 0.9:1 | 29 | 75.3 | 24.5 | 5.5 |
| 6 (Invention) | $FeCl_3$ | ~60 | 0.9:1 | 25 | 80.7 | 19.3 | 4.9 |
| 7 (Invention) | $FeCl_3$ | ~80 | 0.9:1 | 23 | 77.7 | 22.3 | 4.7 |
| 8 (Invention) | $FeCl_3 + SmCl_3$ | ~80 | 0.9:1 | 25 | 84.0 | 16.0 | 4.6 |
| 9 (Invention) | $FeCl_3 + CeCl_3$ | ~130 | 1.0:1 | 31 | 88.8 | 11.2 | 3.8 |
| 10 (Invention) | $CeCl_3$ | ~135 | 0.8:1 | 35 | 90.2 | 9.7 | 3.7 |
| 11 (Invention) | $MoCl_5$ | ~75 | 0.9:1 | 48 | 88.3 | 11.6 | 3.6 |

[1]Yield of product ÷ conversion × 100
[2]iodochlorobenzenes
[3]dichlorobenzenes
[4]ratio of para-iodochlorobenzene to ortho-iodochlorobenzene
[5]believed to be erroneous since GLC data for earlier samples from the same run gave ratios of 5.7–5.9.

pounds include iodobenzene, ortho- and para-iodotoluene, 1-iodo-4-ethylbenzene, iodonaphthalenes, iodonitrobenzenes, iodophenols, iodocresols, iodobenzoic acids and ethers thereof and the like. Formed iodination components product can be separated from the reaction mixture by any suitable separation means (preferably fractional distillation). Unreacted aromatic feed compounds can be recycled to the reactor.

The following examples are presented to further illustrate this invention and are not to be considered as unduly limiting the scope of this invention.

EXAMPLE I

This example illustrates the reaction of chlorobenzene with a mixture of free iodine and free chlorine, in the presence of various metal chloride catalysts, so as to produce iodochlorobenzenes.

100–150 mL (1.0–1.5 mol) of chlorobenzene, about 50 grams (0.2 mol) of iodine, about 5–10 grams (0.03–0.06 mol) of either $AlCl_3$ or $SbCl_5$ $MoCl_5$ or $FeCl_3$ or $CeCl_3$ or a mixture of $FeCl_3$ and a lanthanide chloride were added to a glass reactor. This mixture was stirred at a temperature ranging from about 10° C. to about 140° C., depending on the catalyst system used, while about 15–28 grams (0.21–0.39 mol) of chlorine was introduced into the mixture during a time period of about 20 to 60 minutes. The mol ratio of $I_2$ to chlorobenzene was about 0.2:1 in all runs.

The reaction product was analyzed by gas-liquid chromatography (GLC) employing a Hewlett-Packard HP5880 instrument equipped with a flame ionization detector and a capillary absorption column (length: 50 m) the inside wall of which was coated with crosslinked methylsilicone. The column was held at 50° C. for 8 minutes, and then heated at a rate of 10° C./minute to Data in Table I clearly show that
(1) the conversion of chlorobenzene was higher, at comparable reaction conditions, for $FeCl_3$ or $CeCl_3$ or $MoCl_5$ than for $AlCl_3$ or $SbCl_5$ as catalyst;
(2) the selectivity to iodo-chlorobenzenes was higher, at comparable reaction conditions, for $FeCl_3$ or $CeCl_3$ or $MoCl_5$ than for $AlCl_3$ or $SbCl_5$ as catalyst;
(3) conversion and selectivity to iodo-chlorobenzenes were increased when a lanthanide chloride ($SmCl_3$, $CeCl_3$) was added to the $FeCl_3$ catalyst,
(4) the ratio of para-iodochlorobenzene to ortho-iodochlorobenzene was approximately the same for control and invention runs.

The combination of high selectivity to iodo-chlorobenzenes and high ratio of para- to ortho-iodochlorobenzene is most desirable because this means that the yield of p-iodochlorobenzene (1-iodo-4-chlorobenzene) is high. Para-iodochlorobenzene can be reacted with copper metal so as to form 4,4'-dichlorobiphenyl, which is useful as a monomer for the production of poly(biphenylene sulfide), e.g., substantially in accordance with the procedure described in U.S. Pat. No. 3,354,129.

EXAMPLE II

This example illustrates the iodination of chlorobenzene with iodine monochloride as the iodination agent. Experimental tests were carried out substantially in accordance with the procedure described in Example I, except that ICl was used in lieu of iodine and chlorine. The amount of iodine monochloride was 10–15 mole-% ICl in Run 12 and 20–25 mole-% in run 13. Pertinent test results are summarized in Table II.

TABLE II

| Run | Catalyst | Temp. (°C.) | % Conversion of Chlorobenzene | % Selectivity[1] to I—Ph—Cl[1] | % Selectivity[1] to Cl—Ph—Cl[1] | Ratio of p- to o-I—Ph—Cl[1] |
|---|---|---|---|---|---|---|
| 12 (Invention) | $FeCl_3$ | ~65 | 11 | 81.6 | 18.2 | 4.8 |
| 13 (Invention) | $FeCl_3 + SmCl_3$ | ~65 | 24 | 84.2 | 15.7 | 4.8 |

[1]ratio of para-iodochlorobenzene to ortho-iodochlorobenzene.

Test data in Table II show that iodochlorobenzene compounds were formed at high selectivity in the iodination of chlorobenzene with ICl. The ratio of para-iodochlorbenzene to ortho-iodochlorobenzene was generally higher than for the iodination with iodine and chlorine (see Table I). Both conversion and selectivity to iodochlorobenzene compounds were enhanced when a lanthanide chloride, $SmCl_3$, was added to the $FeCl_3$ catalyst.

EXAMPLE III

This example illustrates the reaction of fluorobenzene with a mixture of free iodine and free chlorine, in the presence of various metal halide catalysts, so as to produce iodo-fluorobenzenes.

100-200 mL (1.1-2.1 mol) of fluorobenzene, about 50-100 grams (0.2-0.4 mol) of iodine, about 5-7 grams (0.03-0.04 mol) of $FeCl_3$ and, optionally, 1.0 grams of $CeCl_3$ were added to a glass reactor. This mixture was stirred at a temperature of about 35°-80° C. while about 15-35 grams (0.2-0.5 mole) of chlorine was added into the reaction mixture during a period of about 30-60 minutes.

The reaction product was analyzed essentially in accordance with the procedure described in Example I. GLC retention times were: 5.2 minutes for fluorobenzene, 14.9 minutes for para-iodofluorobenzene and 15.5 minutes for ortho-iodofluorobenzene. No meta-iodo-compounds were detected. Pertinent test data are summarized in Table III.

reagent. Para-iodofluorobenzene can be reacted with Cu to form 4,4'-difluorobiphenyl, which is useful as a monomer for the production of poly(biphenylene sulfide).

EXAMPLE IV

This example illustrates the iodination of dihalobenzene, trihalobenzene, xylene, nitrobenzene and ethyl benzoate with a mixture of free iodine and chlorine, in the presence of $FeCl_3$, optionally containing a lanthanide chloride, as catalyst. The reaction was carried out substantially in accordance with the procedure outlined in Example I. Pertinent test results are summarized in Table IV.

TABLE IV

| Run | Organic Feed Compound | Catalyst | Temp. (°C.) | Mol Ratio of $I_2:Cl_2$ | % Conversion of Feed Comp. | % Selectivity to Iodo Compounds | % Selectivity to Chloro Compounds |
|---|---|---|---|---|---|---|---|
| 22 (Invention) | 1,2-dichlorobenzene | $FeCl_3$ | 65 | 0.8:1 | 27 | 74 | 26 |
| 23 (Invention) | 1,2,4-Trichlorobenzene | $FeCl_3$ | 110-140 | 1.1:1 | 45 | 67 | 33 |
| 24 (Invention) | xylene[1] | $FeCl_3$ | 35 | 0.9:1 | 21 | 58 | 42 |
| 25 (Invention) | Nitrobenzene | $FeCl_3$ | 75 | 0.9:1 | 3 | 43 | 57 |
| 26 (Invention) | Ethyl Benzoate | $FeCl_3$ + $SmCl_3$ | 95 | 1.0:1 | 11 | 61 | 39 |

[1] a mixture of ortho-, meta- and p-xylenes.

Data in Table IV shows that iron(III) chloride, optionally containing a lanthanide chloride, was effective in catalyzing the iodination of various substituted aromatic feed compounds. Based on these test results, it is believed that the combination of $FeCl_3$ and lanthanide chloride (in particular $SmCl_3$) is also effective in catalyzing the iodination of these aromatic feed compounds with ICl as the iodination reagent.

Reasonable variations and modifications are possible within the scope of the disclosure and the appended claims.

I claim:

1. An iodination process comprising the step of contacting

TABLE III

| Run | Catalyst | Temp. (°C.) | Mol Ratio of $I_2:Cl_2$ | % Conversion of Fluorobenzene | % Selectivity[1] to I—Ph—F[2] | % Selectivity[1] to Cl—Ph—F[3] | Ratio of p- to o-I—Ph—F[4] |
|---|---|---|---|---|---|---|---|
| 14 (Invention) | $FeCl_3$ | ~60 | 0.9:1 | 38 | 77.0 | 23.0 | 12.0 |
| 15 (Invention) | $FeCl_3$ + $CeCl_3$ | ~60 | 0.9:1 | 45 | 92.8 | 5.9 | 11.2 |
| 16 (Invention) | $FeCl_3$ + $CeCl_3$ | ~35 | 0.9:1 | 63 | 76.0 | 24.0 | 14.2 |
| 17 (Invention) | $FeCl_3$ + $CeCl_3$ | ~50 | 0.9:1 | 87 | 89.3 | 8.8 | 12.5 |
| 18 (Invention) | $FeCl_3$ + $CeCl_3$ | ~70 | 0.9:1 | 70 | 85.7 | 13.3 | 11.4 |
| 19 (Invention) | $FeCl_3$ + $CeCl_3$ | ~80 | 0.9:1 | 81 | 85.2 | 12.1 | 10.1 |
| 20 (Invention) | $MoCl_5$ | ~25 | 0.9:1 | 28 | 64.5 | 35.5 | 11.4 |
| 21 (Invention) | $MoCl_5$ | ~75 | 0.9:1 | 45 | 81.7 | 18.0 | 7.9 |

[1] Yield of product to ÷ conversion × 100
[2] iodofluorobenzenes
[3] chlorofluorobenzenes
[4] ratio of para-iodofluorobenzene to ortho-iodofluorobenzene
[5] Note: Mole ratio of fluorobenzene to iodine was about 3:1 in run 11, about 2:1 in run 12 and about 0.6:1 in runs 13–16.

Test data in Table III show that the conversion of fluorobenzene and the selectivity to iodo-fluorobenzenes, were increased when cerium chloride was added to a $FeCl_3$ catalyst. Increasing the reaction temperature resulted in enhanced conversion and generally also in enhanced selectivity to iodo-fluorobenzenes. The ratio of the desirable para-iodofluorobenzene to ortho-iodofluorobenzene was quite high: 8-14.

Based on the above-described test results, it is believed that the combination of $FeCl_3$ and lanthanide chloride (in particular $CeCl_3$) is also more effective than $FeCl_3$ alone in catalyzing the iodination of fluorobenzene to para- and ortho-iodofluorobenzenes (in particular p-iodofluorobenzene) with ICl as the iodination (a) a feed stream comprising at least one monohalobenzene compound with (b) an iodination reagent selected from the group consisting of (i) iodine monochloride (ii) mixtures of free iodine and free chloride having an $I_2:Cl_2$ mol ratio in the range of from about 1:3 to about 3:1, and (c) a catalyst composition comprising at least one material selected from the group consisting of lanthanide chlorides, mixtures of iron(III) chloride with cerium chloride and mixtures of iron(III) chloride with samarium chloride;

under such iodination conditions as to obtain a product comprising at least one para-iodohalobenzene compound;
wherein the weight ratio of iron(III) chloride to cerium chloride in said mixtures of iron(III) chloride with cerium chloride is in the range of from about 1:10 to about 20:1, and the weight ratio of iron(III) chloride to samarium chloride in said mixtures of iron(III) chloride with samarium chloride is in the range of from about 1:10 to about 20:1.

2. A process in accordance with claim 1, wherein said at least one monohalobenzene compound is chlorobenzene, and said product comprises para-iodochlorbenzene.

3. A process in accordance with claim 1, wherein said at least one monohalobenzene compound is fluorobenzene, and said product comprises para-iodofluorobenzene.

4. A process in accordance with claim 1, wherein said $I_2:Cl_2$ mol ratio is in the range of from about 1:2 to about 2:1.

5. A process in accordance with claim 1, wherein said catalyst composition consists essentially of $CeCl_3$.

6. A process in accordance with claim 1, wherein the catalyst composition is selected from the group consisting of mixtures of $FeCl_3$ and $CeCl_3$ having a $FeCl_3:CeCl_3$ weight ratio of about 1:10 to about 20:1, and of mixtures of $FeCl_3$ and $SmCl_3$ having a $FeCl_3:SmCl_3$ weight ratio of about 1:10 to about 20:1.

7. A process in accordance with claim 1, wherein said iodination reagent is (i) ICl, and the mol ratio of said monohalobenzene compound to ICl is in the range of from about 100:1 to about 1:3.

8. A process in accordance with claim 7, wherein said monohalobenzene compound is selected from the group consisting of chlorobenzene and fluorobenzene, and said mol ratio of said monohalobenzene compound to ICl is in the range of from about 10:1 to about 1:1.

9. A process in accordance with claim 1, wherein said iodination reagent is (ii) a mixture of $I_2$ and $Cl_2$ having an $I_2:Cl_2$ mol ratio in the range of from about 1:2 to about 2:1, and the mol ratio of said monohalobenzene compound to $I_2$ is in the range of from about 100:1 to about 1:3.

10. A process in accordance with claim 9, wherein said monohalobenzene compound is selected from the group consisting of chlorobenzene and iodobenzene, and said mol ratio of said monohalobenzene compound to $I_2$ is in the range of from about 10:1 to about 1:1.

11. A process in accordance with claim 1, wherein said iodination reaction conditions comprise a mol ratio of said at least one monohalobenzene compound to said catalyst composition in the range of from about 200:1 to about 2:1, a reaction temperature in the range of from about 0° C. to about 200° C. and a reaction time in the range of from about 1 second to about 20 hours.

12. A process in accordance with claim 1, comprising the additional step of separating said at least one para-iodohalogen compound from said product.

13. A process in accordance with claim 1, wherein said iodination reaction conditions comprise a mol ratio of said at least one monohalobenzene compound to said catalyst composition in the range of from about 100:1 to about 10:1, a reaction temperature in the range of from about 10° C. to about 150° C. and a reaction time in the range of from about 0.01 to about 2 hours.

14. A process in accordance with claim 6, wherein said $FeCl_3:CeCl_3$ weight ratio is about 1:2 to about 10:1, and said $FeCl_3:SmCl_3$ weight ratio is about 1:2 to about 10:1.

* * * * *

UNITED STATES PATENT AND TRADEMARK OFFICE
CERTIFICATE OF CORRECTION

PATENT NO. : 4,716,254
DATED : 12/29/87
INVENTOR(S) : Raymond L. Cobb

It is certified that error appears in the above-identified patent and that said Letters Patent are hereby corrected as shown below:

Column 8, line 60, claim 1, insert ---and--- after "monochloride".

Signed and Sealed this

Twenty-fourth Day of May, 1988

Attest:

DONALD J. QUIGG

Attesting Officer

Commissioner of Patents and Trademarks